United States Patent [19]

Wang et al.

[11] Patent Number: 5,508,038
[45] Date of Patent: Apr. 16, 1996

[54] POLYISOBUTYLENE ADHESIVES FOR TRANSDERMAL DEVICES

[75] Inventors: Karly S. Wang, Newark; James L. Osborne, Mountain View; James A. Hunt, Fremont; Melinda K. Nelson, Sunnyvale, all of Calif.

[73] Assignee: Alza Corporation, Palo Alto, Calif.

[21] Appl. No.: 509,644

[22] Filed: Apr. 16, 1990

[51] Int. Cl.⁶ ..................................... A61L 15/00
[52] U.S. Cl. .................... 424/448; 424/449; 525/191; 526/348.7
[58] Field of Search ................... 424/448, 449; 526/348.7; 525/191

[56] References Cited

U.S. PATENT DOCUMENTS

| | | | |
|---|---|---|---|
| 3,252,802 | 5/1966 | Cunningham | 514/343 |
| 3,433,775 | 3/1969 | Ray et al. | 526/348.7 |
| 3,598,122 | 8/1971 | Zaffaroni | 128/268 |
| 3,598,123 | 8/1971 | Zaffaroni | 128/268 |
| 3,721,661 | 3/1973 | Susa | 526/348.7 |
| 3,731,683 | 5/1973 | Zaffaroni | 128/268 |
| 3,734,097 | 5/1973 | Zaffaroni | 128/268 |
| 3,845,217 | 10/1974 | Ferno et al. | 426/3 |
| 3,870,794 | 3/1975 | Hutchinson et al. | 514/347 |
| 3,877,468 | 4/1975 | Lichtneckert et al. | 131/959 |
| 3,923,939 | 12/1975 | Baker et al. | 264/49 |
| 3,926,188 | 12/1975 | Baker et al. | 128/156 |
| 3,996,245 | 12/1976 | Hartog et al. | 260/340.9 |
| 4,031,894 | 6/1977 | Urquhart et al. | 424/449 |
| 4,060,084 | 11/1977 | Chandrasekaran et al. | 128/260 |
| 4,125,623 | 11/1978 | Hartog et al. | 424/278 |
| 4,144,317 | 3/1979 | Higuchi et al. | 128/260 |
| 4,152,499 | 5/1979 | Boezel et al. | 526/348.7 |
| 4,201,211 | 5/1980 | Chandrasekaran et al. | 128/268 |
| 4,262,003 | 4/1981 | Urquhart et al. | 424/267 |
| 4,286,592 | 9/1981 | Chandrasekaran | 128/260 |
| 4,379,454 | 4/1983 | Campbell et al. | 424/449 |
| 4,425,337 | 1/1984 | Alexander et al. | 424/181 |
| 4,440,740 | 4/1984 | Fix et al. | 424/1.1 |
| 4,562,075 | 12/1985 | Rajadhyaksha | 514/788 |
| 4,573,995 | 3/1986 | Cheng et al. | 424/449 |
| 4,597,961 | 7/1986 | Etscorn | 424/448 |
| 4,623,346 | 11/1986 | von Bittera et al. | 424/448 |
| 4,627,852 | 12/1986 | von Bittera et al. | 424/449 |
| 4,647,580 | 3/1987 | Roszkowski | 514/464 |
| 4,665,069 | 5/1987 | Rosenberg | 514/222 |
| 4,680,172 | 7/1987 | Leeson | 424/448 |
| 4,715,387 | 12/1987 | Rose | 131/270 |
| 4,748,181 | 5/1988 | Hutchinson et al. | 514/343 |
| 4,758,434 | 7/1988 | Kydonieus et al. | 424/449 |
| 4,776,850 | 10/1988 | Guse et al. | 424/485 |
| 4,797,284 | 1/1989 | Loper et al. | 424/449 |
| 4,839,174 | 6/1989 | Baker et al. | 424/448 |
| B1 3,598,122 | 11/1982 | Zaffaroni | 128/268 |
| B1 3,742,951 | 11/1982 | Zaffaroni | 128/268 |
| B1 4,588,580 | 1/1989 | Gale et al. | 424/449 |

FOREIGN PATENT DOCUMENTS

| | | | |
|---|---|---|---|
| 57457/86 | 11/1986 | Australia | A61K 9/70 |
| 81454/87 | 5/1988 | Australia | A61K 9/66 |
| 0190814 | 8/1966 | European Pat. Off. | A61L 15/06 |
| 0117027 | 8/1984 | European Pat. Off. | A61M 37/00 |
| 0186071 | 7/1986 | European Pat. Off. | A61L 15/03 |
| 0204968A1 | 12/1986 | European Pat. Off. | |
| 0251425 | 1/1988 | European Pat. Off. | A61K 9/00 |
| 0374980 | 6/1990 | European Pat. Off. | |
| 3438284 | 3/1985 | Germany | A81K 31/485 |
| 1251619A | 4/1985 | Japan . | |
| 2171906 | 9/1986 | United Kingdom | A61K 9/00 |
| 8702870A | 5/1987 | WIPO . | |
| 88/01516 | 3/1988 | WIPO . | |

OTHER PUBLICATIONS

Protective Clothing as a Means of Reducing Nicotine Absorption in Tobacco Harvesters; S. H. Gehlbach, M. D., W. A. Williams, B.S., J. I. Freeman, D.V.M. Archives of Environmental Health, Mar./Apr. 1979, pp. 111–114.

A Simplified Procedure for the Gas Chromatographic Determination of Nicotine: Application of the Method to Mouse Skin; C. Carruthers and A. Neilson Mikrochimica Acta (Wien) 1980 II, pp. 59–66.

Nicotine, Resorption and Fate; H. Schievelbein Pharmac. Ther. vol. 18. pp. 233–248 (1982).

Transdermal Administration of Nicotine; J. E. Rose, M. E. Jarvik and K. D. Rose Drug and Alcohol Dependence, 13 (1984) 209–213, Elsevier Sci. Pubs. Ireland.

Transdermal Nicotine Reduces Cigarette Craving and Nicotine Preference; Jed E. Rose, Ph.D., Joseph E. Herskovic, Ph.D., Yvonne Trilling, and Murray Jarvik, M.D., Ph.D., Clin Pharmacol Ther. (Oct. 1985) vol. 38, No. 4.

6th World Conference on Smoking and Health, Abstracts, Nov. 9–12, 1987; Tokyo, Japan.

*Primary Examiner*—D. Gabrielle Phelan
*Attorney, Agent, or Firm*—Steven F. Stone

[57] ABSTRACT

An in-line adhesive, useful for transdermal delivery devices comprising a mixture of high and low molecular weighted polyisobutylene having a ratio HMW PIB:LMW PIB in the range of about 5–40:95–60 which is substantially free of plasticizers and tackifiers is disclosed. The adhesive finds particular use as a component of a transdermal delivery device for delivering oily non-polar agents such as nicotine, benztropine, secoverine, dexsecoverine, and arecoline.

20 Claims, No Drawings

5,508,038

POLYISOBUTYLENE ADHESIVES FOR TRANSDERMAL DEVICES

TECHNICAL FIELD

The invention herein pertains to polyisobutylene (PIB) adhesives useful in transdermal drug delivery systems.

BACKGROUND ART

Transdermal devices for delivery of a variety of biologically active agents through the skin or mucosa are known to the art. Representative systems which use rate controlling membranes and in-line adhesives (i.e., adhesives disposed in the path of drug or agent migration from the reservoir to the skin) are disclosed in U.S. Pat. Nos. 3,598,122; 3,598,123; 3,742,951; 4,031,894; 4,060,084; 4,144,317; 4,201,211; and 4,379,454. Subsaturated transdermal devices are disclosed in U.S. Pat. No. 4,379,454. U.S. Pat. No. 4,286,592 describes a transdermal drug delivery device in which the PIB/MO adhesive is less permeable to the drug being delivered than is the reservoir layer. The limited permeability adhesive layer acts as a rate-controlling member.

When in-line adhesives are used in transdermal delivery devices it is necessary that they exhibit a reasonable permeability to the agent being delivered and, when they are used in combination with a rate-controlling membrane, the adhesive layer preferably exhibits a higher permeability to the drug than the rate controlling membrane.

Mixtures of high and low molecular weight polyisobutylenes (PIB) are known to the art as adhesives, however they are relatively impermeable to many drugs. As a result, the prior art in-line PIB adhesives usually contain a plasticizer such as mineral oil (MO) or polybutene to achieve sufficient permeability to permit drug migration through the adhesive at rates which are therapeutically useful from reasonably sized systems.

A typical formulation of the prior art uses a ratio of 1.2M molecular weight (MW) PIB:35K MW PIB:MO of about 1:1.125:2. In such a formulation the high molecular weight (HMW) PIB acts as an adhesive base, the low molecular weight (LMW) PIB acts as tackifier, and the mineral oil acts to plasticize the adhesive and to increase the permeability of the adhesive composition to the drug.

It is also known to include tackifiers to improve the adhesive characteristics of medical adhesives. For example, Australian application AU-A-57457/86 discloses a self adhesive matrix for delivering nitroglycerin which comprises a mineral oil-free mixture of high and low molecular weight PIB's with a resinous tackifier. Such tackifiers are often natural resinous or rosinous products of undefined compositions. Both mineral oil and tackifiers vary in their detailed composition from batch to batch and may unpredictably contain components which are irritating or sensitizing to the skin.

Many medically acceptable contact adhesives of the prior art are ineffective in the transdermal delivery of active agents which are highly soluble in the adhesives. When the agent has a high solubility in the adhesive layer, substantial quantities of agent migrate from the reservoir through the rate controlling membrane and into the adhesive layer as the device equilibrates over time. The migration continues until the thermodynamic activity of the agent in the adhesive equals the thermodynamic activity of the agent in the reservoir. As a result, the large quantity of the active agent in the adhesive layer is released onto the skin without control by the rate controlling membrane, which can only exert an effect on the agent which remains in the reservoir. High concentrations of agent in direct contact with the skin can also cause irritation, or produce undesirably high initial plasma levels of the agent.

Many medically acceptable contact adhesives of the prior art are also ineffective in conjunction with agents which are capable of plasticizing, solvating, or otherwise causing the adhesive to lose its cohesiveness. Such agents, which are typically oily, non-polar components such as nicotine, benztropine, secoverine, dexsecoverine and arecoline, for example, can destroy the adhesive properties of a transdermal patch, causing premature detachment of the system. U.S. Pat. Nos. 4,597,961 and 4,839,174, the disclosures of which are incorporated herein by reference, disclose transdermal nicotine delivery devices in which nicotine is present in the reservoir. The device of U.S. Pat. No. 4,597,561 uses a peripheral adhesive to avoid this type of problem. Copending, commonly assigned U.S. application Ser. No. 07/206,546, filed Jun. 14, 1988 now abandoned, the disclosure of which is incorporated herein by reference, describes a transdermal nicotine delivery system using a subsaturated reservoir to cope with this problem.

Mineral oil is also soluble in some common components of transdermal systems, such as ethylene vinyl acetate copolymers (EVA) and may migrate from the adhesive layer into these materials over time. The loss of the plasticizing mineral oil in the adhesive can cause changes in the physical properties of the adhesive compound, adversely affecting the performance of the adhesive.

According to our invention, it has unexpectedly been discovered that certain agents, in the presence of which traditional transdermal non-PIB adhesives are plasticized, solvated, or lose their adhesive properties, can be delivered from a transdermal delivery device using the in-line PIB adhesives of this invention which are substantially free of tackifiers and plasticizers.

It is therefore an object of this invention to provide a new and useful in-line adhesive for use in transdermal delivery devices.

It is another object of this invention to provide in-line adhesives for transdermal delivery devices which are useful in delivery of agents which have an undesirably high solubility in prior in-line adhesives.

It is another object of the invention to provide a PIB adhesive substantially free of plasticizers and tackifiers.

It is yet another object of this invention to provide an in-line adhesive in a transdermal delivery device which rapidly reaches equilibrium after manufacture.

It is yet another object of the invention to provide a transdermal delivery system using high and low molecular weight PIB substantially free of plasticizers and tackifiers, as an in-line adhesive.

It is another object of this invention to provide PIB adhesives substantially free of plasticizers and tackifiers having a high permeability for the agent to be delivered, and which are suitable as an in-line adhesives in transdermal delivery devices having a release rate controlling membrane.

It is another object of this invention to provide an in-line adhesive for use in a transdermal delivery device which is relatively non-irritating, is inexpensive, can be used in the delivery of oily, non-polar active agents.

BRIEF DESCRIPTION OF THE INVENTION

The invention comprises an adhesive which is useful as an in-line adhesive in transdermal delivery devices. The adhesive comprises mixtures of high molecular weight (HMW) and low molecular weight (LMW) PIBs in weight ratios of about 5–40 HMW PIB:95–60LMW PIB which are substantially free of plasticizers and tackifiers. In use, the adhesive will also contain dissolved active agent at a concentration which is in equilibrium with the concentration of agent in the reservoir.

The adhesive finds particular use as a component of a transdermal delivery device for delivery of active agents which solvate, plasticize, or adversely affect the adhesive properties of conventional in-line adhesives. Such agents include nicotine, benztropine, secoverine, dexsecoverine, or arecoline for example.

DISCLOSURE OF INVENTION INCLUDING BEST MODE

The adhesives of this invention are in-line adhesives for transdermal delivery devices, i.e., the agent being delivered by the system is transported through the adhesive prior to reaching the surface of the skin. In its broadest application, the adhesives of this invention can be used in monolithic transdermal delivery devices which comprise a thin film of the agent dispersed in the adhesive which is normally provided with a protective, agent-impermeable backing layer. In this embodiment, the adhesive layer functions as both the agent reservoir and the adhesive.

The adhesives of this invention could also be used as release rate-controlling adhesives such as are shown in U.S. Pat. No. 4,286,592 which is incorporated herein by reference, in which an adhesive coating on the drug reservoir functions to control release rate and maintain the device on the skin.

The characteristics of the adhesives of this invention, however, make them particularly useful as in-line adhesives in rate controlled transdermal delivery devices which generally comprise, an adhesive layer, a reservoir containing the agent to be delivered and rate-controlling means disposed between the reservoir and adhesive and an agent-impermeable backing layer. A strippable release liner preferably covers the adhesive layer during storage of the device and is removed prior to use. Transdermal delivery devices are applied to a patient for a predetermined administration period, which can range from several hours up to a week depending upon the agent being delivered and the condition being treated.

The term, "agent" as used herein refers to any beneficial agent or compound that can be delivered by a device herein to produce a beneficial and useful result. The term includes medicines, organic and inorganic drugs, hormones, nutrients, vitamins, food supplements, and other agents that benefit an animal or human. It is to be understood that more than one agent may be delivered from a device using the adhesives of this invention, and that the use of the term "agent" in no way excludes the use of two or more such agents.

The term, "plasticizer" as used herein refers to compounds other than the agent being delivered, such as mineral oil, polybutene oil, and other low molecular weight hydrocarbons that act to plasticize PIB adhesives and increase their permeability to the agent being delivered. An adhesive composition is substantially free of plasticizer if it contains, at most, trace amounts of plasticizer and more preferably, no plasticizer.

The term, "tackifier" as used herein refers to materials other than PIB that are added to adhesives to increase their tack or stickiness. Such materials are typically natural occurring resinous or rosinous materials or truly synthetic polymer materials. An adhesive is substantially free of tackifier if it contains, at most, trace amounts of tackifier and preferably no tackifier.

The term, "high molecular weight polyisobutylene" (HMW PIB) refers to a polyisobutylene composition having an average molecular weight in the range of about 450,000 to about 2,100,000, and preferably from about 990,000 to about 1,600,000.

The term, "low molecular weight polyisobutylene" (LMW PIB) refers to a polyisobutylene composition having an average molecular weight in the range of about 1,000 to about 450,000, and preferably from about 35,000 to about 50,000.

The adhesive composition of this invention contains the HMW and LMW PIB in weight ratios (HMW PIB:LMW PIB) in the range of about 5–40:95–60, preferably in the range of about 10–25:90–75 and most preferred in the range of about 10–20:90–80. The ratio of HMW PIB to LMW PIB which provides an optimal adhesive for a specific agent will be dependent upon the identity and concentration of agent being delivered.

It is preferable that extraneous components of the adhesives of this mixture be minimized or eliminated in order to minimize the potential for irritation or allergic reaction when the transdermal delivery system contacts the skin. However dyes, pigments, inert fillers, stabilizers, stiffeners such as colloidal silicon dioxide, or other additives other than plasticizers and tackifiers well known to the art may be added if desired.

The thickness of the adhesive layer will generally be between about 1 mil (0.0254 mm) and about 15 mil (0.381 mm) when used with a rate-controlling membrane. The composition and thickness of the adhesive layer will be adjusted such that the adhesive layer does not constitute a significant permeation barrier to the passage of the agent to be delivered as compared to that of the rate-controlling membrane. Unless the drug involved requires the use of a loading dose to rapidly saturate drug delivery sites in the skin, the thickness is also preferably selected so that the adhesive does not contain a substantial amount and preferably less than about 15% of the total amount of agent in the device, particularly in rate-controlled delivery devices.

Transdermal delivery devices using the adhesives of this invention may be of the monolithic or release rate-controlling adhesive type but are preferably of the release rate-controlling membrane type which comprise rate controlling means between the drug reservoir and the in-line adhesive. The rate-controlling means acts to regulate the flux of the agent being delivered to the skin and the rate controlling element will have a lower permeability to the agent being delivered than the adhesive layer. Materials which are appropriate for use with transdermal delivery systems are given in the patent application U.S. Ser. No. 07/206,546 now abandoned, and in U.S. Pat. Nos. 3,797,494 and 4,031,894, which are incorporated herein by reference.

The reservoir of such a transdermal delivery device contains one or more agents to be delivered, dispersed within a matrix. Suitable materials for the matrix of the reservoir include, without limitation, natural and synthetic rubbers or other polymeric materials, petroleum jelly or aqueous gels. When the agent being delivered is nicotine, a preferred reservoir polymer matrix is fabricated from an ethylene-vinyl acetate (EVA) copolymer such as is described in U.S. Pat. No. 4,144,317, preferably having a vinyl acetate content within the range of about 28 to 60 weight percent. Other embodiments of transdermal delivery devices are known to the art and are also appropriate for use with the adhesives herein. For example, the transdermal delivery devices shown in U.S. Pat. Nos. 3,598,123, and 4,588,580, the disclosures of which are hereby incorporated by reference, can find application with the adhesives disclosed herein.

The permeability of many agents through PIB is relatively low in the absence of a plasticizer and for this reason the in-line PIB adhesives of the prior art contained plasticizers such as mineral oil or polybutene. We have found that certain agents, typically oily, non-polar substances usually liquid at ambient temperatures, have acceptable permeation through the plasticizer-free PIB adhesives of this invention. It was also found that such agents, while highly soluble in typical non-PIB adhesives of the prior art whose adhesive properties are degraded by the concentrations of such agents encountered, exhibit a relatively low solubility in the non-plasticized PIB adhesives of this invention. As a result, the concentration of agent which is present in the adhesive layer upon equilibration is significantly reduced as compared to that observed in prior art non-PIB adhesives. When used with such oily agents, this significantly reduces the degradation caused by the agent, so that the physical integrity and adhesive characteristics of the adhesives of this invention are maintained. Oily, non-polar agents having the desired properties include, without limitation, nicotine, benztropine, secoverine, dexsecoverine and arecoline.

A backing layer prevents passage of the agent through the surface of the reservoir distal to the skin, and provides support for the system, if needed. The backing layer is impermeable or substantially impermeable to the passage of the agent. It can be flexible or nonflexible. Suitable materials are well known to the art and include, without limitation, polyethylene terephthalate, various nylons, polypropylene, metalized polyester films, polyvinylidene chloride, and aluminum foil.

A release liner can be included in the transdermal delivery device as manufactured, as is well known in the art. The release liner is removed before the transdermal delivery device is applied to the skin.

In a preferred embodiment a transdermal delivery device uses a PIB adhesive of this invention together with a subsaturated reservoir including nicotine.

The following examples are illustrative of the present invention and they are not to be construed as limitations of the scope of the invention. Variations and equivalents of these examples will be readily apparent to workers skilled in the art in light of the present disclosure. All ratios and percentages are on a weight basis, and all temperatures are in degrees Celsius, unless otherwise noted.

EXAMPLE 1

PIB adhesives according to this invention were prepared as follows:

Formula A: PIB having a MW of 35K was thoroughly blended with PIB having a MW of 1.2M, in a weight ratio of HMW PIB:LMW PIB of 25:75.

Formula B: PIB having a MW of 35K was thoroughly blended with PIB having a MW of 1.2M, in a weight ratio of HMW PIB:LMW PIB of 20:80.

Formula C: PIB having a MW of 35K was thoroughly blended with PIB having a MW of 1.2M, in a weight ratio of HMW PIB:LMW PIB of 15:85.

Formula D: PIB having a MW of 35K was thouroughy blended with PIB having a MW of 1.2M, in a weight ratio of HMW PIB:LMW PIB of 10:90.

EXAMPLE 2

Subsaturated transdermal drug delivery systems were made by extruding a 0.13 mm thick drug reservoir film comprising a subsaturated solution of 40% nicotine base in 60% EVA (40% VA) between an impermeable, pigmented aluminized polymer backing (Medpar™) and a high density polyethylene (HDPE) rate-controlling membrane 0.05 mm thick. This trilaminate was laminated to adhesives of Formulae B–D of Example 1 that were solvent cast from n-heptane solution onto a 0.076 mm strippable release liner formed of fluorocarbon diacrylate/polyethylene terephthalate, (3M 1022) and allowed to reach equilibrium. All samples exhibited good adhesive properties and had 24 hour average in vitro release rates into water at 37° C. of 60 $\mu g/(cm^2\ hr)$, 70 $\mu g/(cm^2\ hr)$, and 72 $\mu g/(cm^2\ hr)$ respectively.

EXAMPLE 3

The procedures of Example 2 were repeated using the adhesive of Formula A and substituting, as the drug reservoir, a mixture of 70 wt % EVA-40 and 30 wt % nicotine base. The weight percent of the nicotine in the adhesive upon equilibration was found to be about 11 weight percent.

The procedures of Example 2 were repeated, using the adhesive of formula B with the above 70/30 EVA-40-nicotine reservoir. The weight percent of nicotine in the adhesive upon equilibration was also found to be about 11 weight percent.

The procedures of Example 2 were repeated, using the adhesive of Formula B, and reservoir composition of 20%, 30% and 40% nicotine base in EVA-40. The weight percent of nicotine in the PIB adhesive after equilibration was found to be as follows: 8 wt. percent in the 20% nicotine reservoir device; 10 wt. percent in the 30% nicotine reservoir device; and 14 wt. percent in the 40% nicotine reservoir device.

EXAMPLE 4

The procedures of Examples 2 and 3 are repeated substituting a 2 mil (0.0508 mm) low density polyethylene (LDPE) membrane for the HDPE membrane and substituting for the nicotine reservoir solution, 10% benztropine and 90% EVA-40 to produce transdermal devices for the delivery of benztropine.

The devices will exhibit in vitro release rates into water at 37° C. of about 5–15 $\mu g/cm^2\ hr$ and will have good adhesive properties.

EXAMPLE 5

The procedures of Examples 2 and 3 are repeated, substituting for the nicotine reservoir solution, 15% secoverine and 85% EVA-40 to produce transdermal devices for the delivery of secoverine. The devices will exhibit in vitro release rates into water at 37° C. of about 5–15 $\mu g/cm^2\ hr$ and will have good adhesive properties.

EXAMPLE 6

The procedures of Examples 2 and 3 are repeated, substituting for the nicotine reservoir solution, 15% dexsecoverine and 85% EVA-40 to produce transdermal devices for the delivery of dexsecoverine. The devices will exhibit in vitro release rates into water at 37° C. of about 5–15 µg/cm² hr and will have good adhesive properties.

EXAMPLE 7

The procedures of Example 2 and 3 are repeated, substituting for the nicotine reservoir solution, 40% arecoline and 60% EVA-40 to produce transdermal devices for the delivery of arecoline. The device will exhibit in vitro release rates into water at 37° C. of about 50–100 µg/cm² hr and will have good adhesive properties.

While the present invention has been described with respect to certain delivery devices, it will be apparent to one skilled in the art that variations, modifications and substitutions can be made. These variations, modifications and substitutions can be made without departing from the scope of our invention, which is limited only by the following claims.

We claim:

1. A polyisobutylene (PIB) adhesive composition for use in a transdermal active agent delivery device, said adhesive composition comprising an oily, non-polar liquid active agent dissolved in a polymeric component consisting essentially of a mixture of high molecular weight (HMW) PIB having an average molecular weight in the range of about 450,000–about 1,600,000 and low molecular weight (LMW) PIB having an average molecular weight in the range of about 1,000–about 450,000, the ratio HMW PIB:LMW PIB being in the range of 5–40:95–60; said adhesive composition being substantially free of plasticizers and tackifiers.

2. A polyisobutylene adhesive composition for use in a transdermal nicotine delivery device, said adhesive composition comprising nicotine dissolved in a polymeric component consisting essentially of a mixture of HMW PIB having an average molecular weight in the range of about 450,000–about 1,600,000 and LMW PIB having an average molecular weight in the range of about 1,000–about 450,000, the ratio HMW PIB:LMW PIB being in the range of 5–40:95–60; said adhesive composition being substantially free of plasticizers and tackifiers.

3. The composition of claim 1 or 2, wherein said HMW PIB has an average molecular weight in the range of about 990,000–about 1,600,000 and said LMW PIB has an average molecular weight in the range of about 35,000–about 50,000.

4. The composition of claim 3, wherein the ratio of HMW PIB:LMW PIB is in the range of 10–25:90–75.

5. The composition of claim 4, wherein the HMW PIB has an average molecular weight of about 1,200,000 and said LMW PIB has an average molecular weight of about 35,000.

6. The composition of claim 1 or 2 wherein said ratio is in the range of 10–20:90–80.

7. The composition of claim 3 wherein said ratio is in the range of 10–20:90–80.

8. The composition of claim 5 wherein said ratio is in the range of 10–20:90–80.

9. A transdermal delivery device for delivering an oily, non-polar active agent comprising:
a) reservoir means containing said active agent;
b) an in-line adhesive comprising:
(i) a polymeric component consisting essentially of a mixture of high molecular weight (HMW) PIB having an average molecular weight in the range of about 450,000–about 1,600,000 and low molecular weight (LMW) PIB having an average molecular weight in the range of about 1,000–about 450,000, the ratio HMW PIB:LMW PIB being in the range of 5–40:95–60; and
(ii) said active agent;
said adhesive being substantially free of plasticizers and tackifiers; and
c) active agent release rate controlling means disposed between said reservoir means and said in-line adhesive.

10. A transdermal nicotine delivery device comprising:
a) reservoir means containing nicotine as active agent;
b) an in-line adhesive comprising:
(i) a polymeric component consisting essentially of a mixture of HMW PIB having an average molecular weight in the range of about 450,000–about 1,600,000 and LMW PIB having an average molecular weight in the range of about 1,000–about 450,000, the ratio HMW PIB:LMW PIB being in the range of 5–40:95–60; and
(ii) nicotine;
said adhesive being substantially free of plasticizers and tackifiers; and
c) nicotine release rate-controlling means disposed between said reservoir means and said in-line adhesive.

11. The device of claim 9, wherein said active agent is selected from the group consisting of nicotine, benztropine, secoverine, dexsecoverine and arecoline.

12. The device of claim 9, 10 or 11 wherein said adhesive contains no more than about 50% of said active agent in the device.

13. A device for the transdermal administration of nicotine as an active agent, said device comprising:
a) a subsaturated nicotine reservoir containing up to about 40 wt % nicotine; and
b) an adhesive disposed in the path of nicotine migration from said nicotine reservoir to the skin, said adhesive comprising nicotine dissolved in a polymeric component consisting essentially of HMW PIB having an average molecular weight in the range of about 450,000–about 1,600,000 and LMW PIB having an average molecular weight in the range of about 1,000–about 450,000, the ratio of HMW PIB:LMW PIB being in the range of about 5–40:95–60, said adhesive being substantially free of plasticizers and tackifiers.

14. The device of claim 9, 10 or 13 wherein said ratio is in the range of 10–25:90–75.

15. The device of claim 9, 10 or 13 wherein said ratio is in the range of 10–20:90–80.

16. A device according to claim 10, wherein said nicotine release rate-controlling means is high density polyethylene.

17. A device according to claim 15, wherein said active agent reservoir comprises from about 5–40 wt % said active agent.

18. A device according to claim 10, wherein said nicotine reservoir comprises from about 60–95 wt % ethylene vinyl acetate copolymer having a vinyl acetate content of about 40%.

19. A device according to claim 15, wherein said adhesive contains no more than about 15 wt % said active agent.

20. The device of claims 9, 10, 11, 13, 16, or 18 wherein said HMW PIB has an average molecular weight of about 1,200,000 and said LMW PIB has an average molecular weight of about 35,000.

* * * * *